United States Patent
Ferrieri

(10) Patent No.: US 6,486,355 B1
(45) Date of Patent: Nov. 26, 2002

(54) APPLICATION OF CHIRAL CRITICAL CLUSTERS TO ASSYMETRIC SYNTHESIS

(75) Inventor: Richard A. Ferrieri, Patchogue, NY (US)

(73) Assignee: Brookhaven Science Associates LLC, Upton, NY (US)

( * ) Notice: Subject to any disclaimer, the term of this patent is extended or adjusted under 35 U.S.C. 154(b) by 0 days.

(21) Appl. No.: 09/511,960

(22) Filed: Feb. 23, 2000

(51) Int. Cl.$^7$ .......................... C07C 45/00; C07C 33/34; C07C 27/00
(52) U.S. Cl. ..................... 568/312; 568/807; 568/878
(58) Field of Search .................. 568/312, 807, 568/878; 204/153.63, 903, 912; 435/132, 147, 148, 155, 156, 157

(56) References Cited

U.S. PATENT DOCUMENTS

| | | | |
|---|---|---|---|
| 4,734,227 A | 3/1988 | Smith ........................... | 264/13 |
| 4,925,790 A | 5/1990 | Blanch et al. ................. | 435/52 |
| 4,970,093 A | 11/1990 | Sievers et al. ................. | 427/38 |
| 5,158,704 A | 10/1992 | Fulton et al. ................. | 252/309 |
| 5,266,205 A | 11/1993 | Fulton et al. ................. | 210/639 |
| 5,268,442 A | 12/1993 | Bradshaw et al. ............. | 528/25 |
| 5,403,739 A | 4/1995 | Ikushima et al. ............. | 435/280 |
| 5,643,357 A | 7/1997 | Breton et al. ............. | 106/31.25 |
| 5,725,987 A | 3/1998 | Combes et al. ............. | 430/137 |
| 5,914,031 A | 6/1999 | Sentagnes et al. .......... | 208/952 |
| 5,962,744 A | 10/1999 | Ojima et al. ................. | 568/454 |

FOREIGN PATENT DOCUMENTS

WO      WO 92/20812      11/1992

OTHER PUBLICATIONS

Bucciarelli, et al., "Optically Active Trifluoromethylcarbinols as Chiral Solvating Agents for Asymmetric Transformations at a Ring–Nitrogen Atom. Synthesis of Optically Active N–Chloroaziridines and Stereochemical Aspects of Chiral Solvent–Aziridine Solute Complexes," J. Org. Chem., 48:2640–2644 (1983).

Ferrieri, et al., "Investigations of Acetonitrile Solvent Cluster Formation in Supercritical Carbon Dioxide, and Its Impact on Microscale Syntheses of Carbon–11–Labeled Radiotracers for PET," Nuclear Medicine and Biology, 26:443–454 (1999).

Primary Examiner—Samuel Barts
Assistant Examiner—Elvis O. Price
(74) Attorney, Agent, or Firm—Margaret C. Bogosian

(57) ABSTRACT

Disclosed is a composition, a method of making and a method of using critical clusters for asymmetric synthesis using substantially optically-pure chiral solvent molecules in a supercritical fluid. The solvent molecules are capable of forming a multipoint hydrogen bonded solvate as they encage at least one solute molecule. The encaged solute molecule is capable of reacting to form an optically active chiral center. In another aspect, there is disclosed a method of directing the position of bonding between a solute molecule and a ligand involving encaging the solute molecule and the ligand with polar solvent molecules in a supercritical fluid under conditions of temperature and pressure sufficient to change electric charge distribution in the solute molecule. In yet another aspect, disclosed is a method of making pharmaceutical compounds involving encaging a solute molecule, which is capable of forming a chiral center, and a ligand with polar solvent molecules in a supercritical fluid under conditions of temperature and pressure sufficient to change electric charge distribution of the solute molecule. The solute molecule and ligand are then reacted whereby the ligand bonds to the solute molecule forming a chiral center. Also disclosed is a method for racemic resolution using critical clusters involving encaging racemic mixtures of solute molecules with substantially optically-pure chiral solvent molecules in a supercritical fluid under conditions of temperature and pressure sufficient to form critical clusters. The solvent molecules are capable of multipoint hydrogen bonding with the solute molecules. The encaged solute molecules are then nonenzymatically reacted to enhance the optical purity of the solute molecules.

12 Claims, 8 Drawing Sheets

(1 of 8 Drawing Sheet(s) Filed in Color)

Large Volume Supercritical Fluid Reactor

APPLICATION OF CHIRAL CRITICAL CLUSTERS TO ASSYMETRIC SYNTHESIS

This invention was made with Government support under Contract No. DE-AC02-98CH 10886 awarded by the U.S. Department of Energy. The Government has certain rights to this invention.

BACKGROUND OF INVENTION

The present invention relates to molecular clusters. In particular, the invention relates to compositions, methods of making and methods of using molecular clusters of solvent mixtures in supercritical fluid.

Supercritical fluids are unique states of matter existing above certain temperatures and pressures. As such, these fluids exhibit a high level of functionality and controllability that can influence not only the macrophysical properties of the fluid, but also influence nano-structures of molecules dissolved in them.

Solvent mixtures in supercritical fluids and pressurized liquids are known to form molecular clusters about dilute solute molecules. These molecular clusters can be described as transient molecular cages and can behave as microscopic reactors. Molecular clusters can confine the space through which trapped molecules can diffuse which can increase the odds that trapped molecules might encounter a reactive collision. Organic solvents have the ability to cluster about dilute solute molecules in mixtures of supercritical fluids and pressurized fluids, and confine the space through which these "caged" molecules can diffuse. Under these circumstances, it can be possible to maintain high reaction efficiency with minute, and possibly stoichiometric amounts of reactants.

The degree to which certain organic solvents cluster in supercritical and pressurized fluids has been studied. For example, acetonitrile has been investigated for its potential to cluster in $CO_2$ above and below the critical point for the mixture. The use of solvents in supercritical fluids to affect the reaction kinetics and the yield of products produced from dilute solute reactant molecules has also been studied. For example, the use of acetonitrile in supercritical carbon dioxide has been investigated for its use as a solvent, as it applies to producing useful quantities of radioactive biomolecules for use in Positron Emission Tomography (PET) in connection with the alkylation reaction between methyiodide and L-α-methyl-N-2-propynyl phenylethylamine (nordeprenyl) to yield L-deprenyl.

In WO 92/20812, certain enzymes were used to selectively catalyze the reaction of only one enantiomer of a chiral compound in supercritical carbon dioxide. Specifically, a racemic mixture of a chiral compound was brought into contact with the enzyme that was only capable of reacting with one enantiomer of the mixture. The chiral product that was obtained was enantiomerically pure and easily separated from the reaction mixture by conventional methods such as extraction, crystallization or evaporation.

U.S. Pat. No. 5,403,703 discloses an enzymatic esterification reaction involving a primary terpene secondary alcohol with a higher fatty acid in a reaction medium of supercritical carbon dioxide in the presence of a lipase. Racemic resolution of the primary terpene secondary alcohol having chirality was achieved by first producing a fatty acid ester of the alcohol having an optical purity of almost 100% and then hydrolyzing the fatty acid ester to convert it back to an alcohol having high optical purity. Furthermore, the reaction velocity of the esterification reaction was found to have increased more than six times when the reaction medium was in supercritical carbon dioxide.

None of the technologies mentioned above disclose the use of fluids as a reaction medium under conditions that cause the reactants to form optically active chiral centers which would not form under ordinary reaction conditions. The technologies mentioned above also do not mention controlling chemical reactions by directing the position of bonding between ligands and molecules. Furthermore, the use of critical clusters for drug synthesis formed by directing the position of bonding between ligands and molecules wherein new chiral centers are formed have not been addressed. Finally, the use of critical clusters for racemic resolution reactions without the use of enzymes has not been addressed.

Thus, there is a need for new compositions which can be used to create optically active chiral centers with the advantages of using supercritical fluids. In addition, there is a need to be able to direct the position where ligands bond to molecules in a chemical reaction. Finally, there is a need to be able to make pharmaceutical compounds and perform racemic resolution reactions using critical clusters.

SUMMARY OF THE INVENTION

According to the present invention, it has now been found that molecular clusters formed by the aggregation of substantially optically-pure chiral solvent molecules dissolved in a supercritical fluid and maintained at or close to its critical density can exert certain spatial constraints on encaged solute molecules that allow for the creation of optically active chiral centers as a result of their undergoing a chemical reaction. In addition, certain kinetic control can be exerted over these molecular clusters and encaged reactant solute molecules that allow for control over the position where ligands bond on molecules. It has been found that these qualities can be tuned by adjusting the pressure and/or temperature of the supercritical fluid medium. Finally, pharmaceutical drug synthesis and racemic resolution reactions without the use of enzymes can be accomplished using critical clusters.

One aspect of the invention is directed to a critical cluster for asymmetric synthesis in which the critical cluster contains substantially optically-pure chiral solvent molecules in a supercritical fluid. The solvent molecules are capable of multipoint hydrogen bonding and encaging at least one solute molecule capable of reacting within the cluster to form an optically active chiral center.

Another aspect of the invention is directed to a method of making critical clusters for asymmetric synthesis which includes encaging at least one solute molecule, which is capable of reacting within the critical cluster to form an optically active chiral center, with substantially optically-pure chiral solvent molecules in a supercritical fluid under conditions of temperature and pressure sufficient to form critical clusters. The substantially optically-pure chiral solvent molecules are capable of multipoint hydrogen bonding with the encaged solute molecules.

In yet another aspect, the invention is directed to a method for asymmetric synthesis using critical clusters. This method involves encaging at least one solute molecule with substantially optically-pure chiral solvent molecules in a supercritical fluid under conditions of temperature and pressure sufficient to form critical clusters. The solvent molecules are capable of multipoint hydrogen bonding with the solute molecules. The encaged solute molecules are then reacted within the cluster whereby an optically active chiral center is formed in a product of the reaction.

In a preferred embodiment, the substantially optically-pure chiral solvent molecules of the present invention are secondary alcohol molecules, preferably having from four to about nine carbon atoms. More preferably, the secondary alcohol molecules are selected from the group consisting of S(+)-2-butanol and R(−)-2-butanol. In another embodiment, the solute molecule is benzaldehyde.

In a preferred embodiment, the supercritical fluid that is employed in the present invention is carbon dioxide. The supercritical carbon dioxide is preferably maintained at a pressure from about 71 bar to about 275 bar, more preferably from about 100 bar to about 150 bar, and at a temperature from about 31° C. to about 125° C., more preferably from about 50° C. to about 70° C.

In another embodiment, the conditions of temperature and pressure of the supercritical fluid are sufficient to change the electric charge distribution of the solute molecule(s). The weight percentage of cosolvent and solute in the supercritical fluid is preferably from about 1% to about 20%, more preferably from about 5% to about 15%.

In a further embodiment, the solute molecule employed is benzaldehyde and the product formed which has an optically active chiral center is S(+)benzoin.

The invention is also directed to a method of directing the position of bonding between a solute molecule and a ligand. This method involves encaging the solute molecule and the ligand with polar solvent molecules in a supercritical fluid under conditions of temperature and pressure sufficient to change electric charge distribution in the solute molecule.

In one embodiment, the polar solvent molecules are capable of multipoint hydrogen bonding to the solute molecules. These polar solvent molecules can be chiral and can also be substantially optically-pure. In addition, the polar solvent molecules can be secondary alcohol molecules, preferably having from four to about nine carbon atoms. The secondary alcohol molecules can be selected from the group consisting of S(+)-2-butanol and R(−)-2-butanol.

In a preferred embodiment, the supercritical fluid that is employed with the method of directing the position of bonding between a solute molecule and a ligand is carbon dioxide. The supercritical fluid is preferably maintained at a pressure from about 71 bar to about 275 bar, more preferably from about 100 bar to about 150 bar, and at a temperature from about 31° C. to about 125° C., more preferably from about 50° C. to about 70° C.

The weight percentage of cosolvent and solute in the supercritical fluid is preferably from about 1% to about 20%, more preferably from about 5% to about 15%.

The ligand employed in the method stated above can be a methyl group and the solute molecule to which the methyl group bonds can be ritalinic acid. In such an embodiment, the conditions of temperature and pressure are sufficient for directing the bonding of the methyl group to the oxygen site of the carboxylic acid functional group on ritalinic acid forming the drug ritalin. The methyl group can come from an methylhalide selected from the group consisting of methyliodide and methylbromide. The polar solvent molecule can also be chiral and capable of multipoint hydrogen bonding to ritalinic acid resulting in an substantially optically-pure ritalin product. The polar solvent molecule can be acetonitrile.

In another aspect, the invention is directed to a method of making pharmaceutical compounds using critical clusters. This method involves encaging a solute molecule, which is capable of forming a chiral center, and a ligand with polar solvent molecules in a supercritical fluid under conditions of temperature and pressure sufficient to change electric charge distribution of the solute molecule. The encaged solute molecule and ligand are then reacted whereby the ligand bonds to the solute molecule forming a chiral center.

The polar solvent molecules can be chiral and they can also be substantially optically-pure. In addition, the polar solvent molecules can be capable of multipoint hydrogen bonding to the solute molecule. When the polar molecules are chiral, the chiral center which is formed can be substantially optically-pure. The polar solvent molecules can be secondary alcohol molecules, preferably having from four to about nine carbon atoms. In addition, the secondary alcohol molecules can be selected from the group consisting of S(+)-2-butanol and R(−)-2-butanol.

In a preferred embodiment, the supercritical fluid employed for making pharmaceutical compounds is carbon dioxide. The supercritical carbon dioxide is preferably maintained at a pressure from about 71 bar to about 275 bar, more preferably from about 100 bar to about 150 bar, and at a temperature from about 31° C. to about 125° C., more preferably from about 50° C. to about 70° C.

The weight percentage of cosolvent and solute in the supercritical fluid employed for making pharmaceutical compounds is preferably from about 1% to about 20%, more preferably from about 5% to about 15%.

In one embodiment, the solute molecule is phenylethylamine and the ligand is a methyl group. The methyl group can come from a methylhalide selected from the group consisting of methyliodide and methylbromide. In this embodiment, the conditions of temperature and pressure can be made sufficient to direct the bonding of the methyl group to the alpha position of phenylethylamine to form amphetamine as the product.

In yet another aspect, the invention is directed to a method for racemic resolution using critical clusters. This method involves encaging racemic mixtures of solute molecules with substantially optically-pure chiral solvent molecules in a supercritical fluid under conditions of temperature and pressure sufficient to form critical clusters. The solvent molecules are capable of multipoint hydrogen bonding with the solute molecules. The encaged solute molecules are nonenzymatically reacted to enhance the optical purity of the solute molecules.

In a preferred embodiment, the substantially optically-pure chiral solvent molecules employed in the method for racemic resolution are secondary alcohol molecules, preferably having from four to about nine carbon atoms. More preferably, the secondary alcohol molecules are selected from the group consisting of S(+)-2-butanol and R(−)-2-butanol.

In a preferred embodiment, the supercritical fluid that is employed with the method for racemic resolution using critical clusters is carbon dioxide. The supercritical carbon dioxide is preferably maintained at a pressure from about 71 bar to about 275 bar, more preferably from about 100 bar to about 150 bar, and at a temperature from about 31° C. to about 125° C., more preferably from about 50° C. to about 70° C.

In another embodiment, the conditions of temperature and pressure of the supercritical fluid can be made sufficient to change the electric charge distribution of the solute molecule. The weight percentage of cosolvent and solute in the supercritical fluid is preferably from about 1% to about 20%, more preferably from about 5% to about 15%.

As a result of the present invention, critical clusters can be made in supercritical fluids and used in microscale reactions to influence chemical reactions and form optically active chiral centers.

The present invention is therefore advantageous in that it allows the formation of optically active chiral centers that would not form under ordinary reaction conditions. Other advantages of the present invention include the capacity to direct the position of bonding between ligands and molecules in supercritical fluids by adjusting the pressure and temperature of the supercritical fluid. Still other advantages of the present invention include the potential for new synthetic pathways for producing pharmaceutical compounds such as amphetamine by directing the bonding of a methyl group to the alpha position of phenylethylamine by controlling the temperature and pressure of the reaction. Finally, the present invention provides the advantage of performing racemic resolution reactions in critical clusters without the need to use enzymes.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The claim of this patent contains at least one drawing executed in color.

DETAILED DESCRIPTION OF INVENTION

Figure 1:
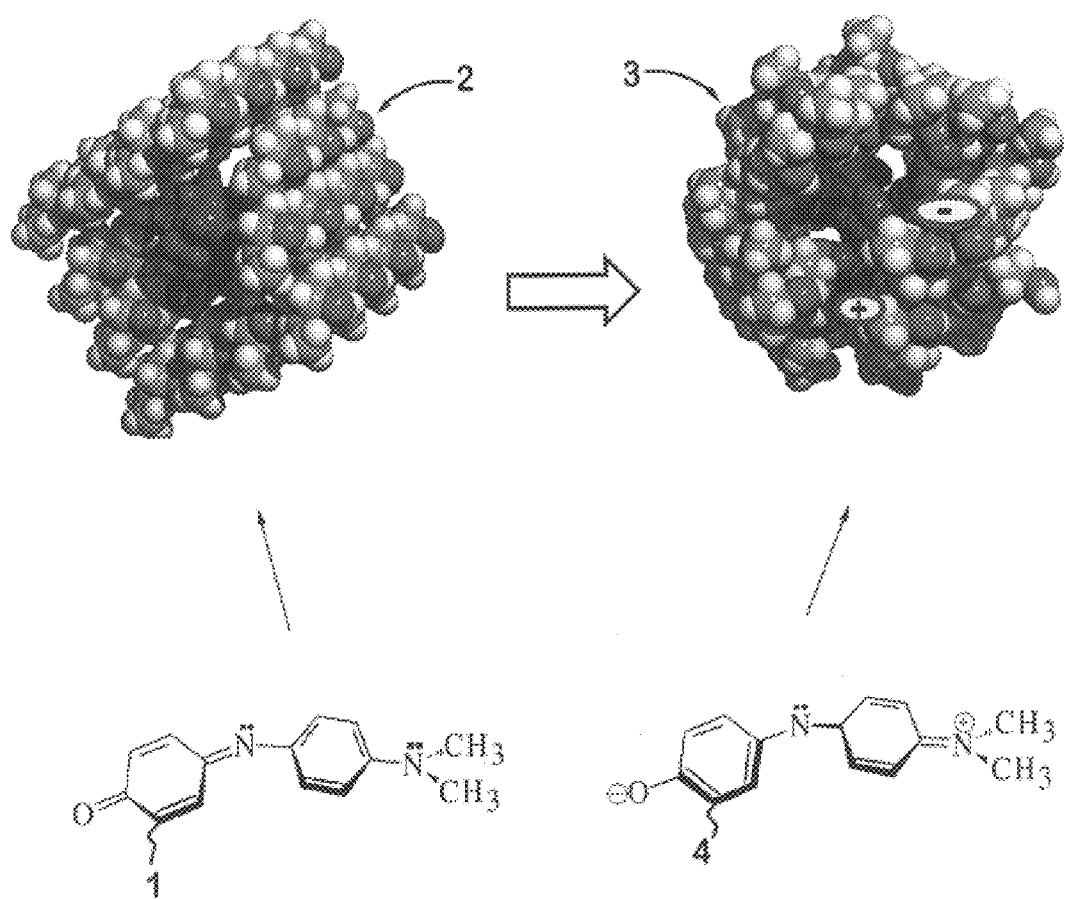
FIG. 1—illustrates a molecular simulation of forty-eight 2-butanol molecules clustered about a single phenol blue molecule in supercritical carbon dioxide.

The present invention is a composition, method of making and method of using critical clusters for asymmetric synthesis using substantially optically-pure chiral solvent molecules. The present invention also provides a method of directing the position of bonding between ligands and molecules using critical clusters, a method of making pharmaceutical compounds using critical clusters and a method for racemic resolution reactions using critical clusters. The general strategy here capitalizes on the ability of organic solvent molecules to cluster about dilute solute molecules in mixtures of supercritical fluids and pressurized liquids, and confine the space through which these "encaged" molecules might encounter a reactive collision. Under these circumstances, it can be possible to maintain high reaction efficiency with minute, and possibly stoichiometric amounts of reactants. Solvent clustering creates localized regions of high density in supercritical fluid because in and around the critical region, a fluid, or fluid mixture, becomes highly compressible.

The present invention is highly unique in that it utilizes the stereochemistry and physical characteristics of molecules under particular temperatures and pressures to form new molecular clusters and to manipulate chemical reactions to form products that would not form under ordinary circumstances.

Supercritical fluids are unique states of matter existing above certain temperatures and pressures. These fluids exhibit a high level of functionality and controllability that can influence not only the macrophysical properties of fluids, but also influence the nano-structures of molecules dissolved in them. The invention relies on the ability of solvent mixtures in supercritical fluids to form molecular clusters about one or more solute molecules, and affect the way these encaged molecules react chemically.

Clustering of polar solvent molecules about one or more solute molecules to form solvent cages occurs with electric charge alignment (dipole alignment) of solvent molecules. This can result in a change in the electric charge distribution of the encaged solute molecules, and more intense solvent-solute interaction. This action can influence cluster structuring and chemical reactions which occur within the cluster. The change in electric charge distribution can either be a charge resonance wherein there is a uniform distribution of charge or electric charge separation wherein the charge is localized. Solvent cages generally possess limited lifetimes of less than 10 nanoseconds in duration. For a solvent cage to have an impact on a chemical reaction occuring within it, it is preferred that the chemical reaction occur in a time frame less than the lifetime of the solvent cages.

A critical cluster for asymmetric synthesis can be made using substantially optically-pure chiral solvent molecules, at least one solute molecule and a supercritical fluid. The terminology "substantially optically-pure chiral solvent molecules" as used herein refers to chiral solvent molecules comprising at least about 70% of one enantiomer of the chiral solvent molecule, preferably greater than 90% of one enantiomer of the chiral solvent molecule and more preferably greater than 98% of one enantiomer of the chiral solvent molecule. A supercritical fluid is any gas at or above its critical point defined by a critical pressure and critical temperature for that substance. When solvent and solute molecules are in a supercritical fluid, the solvent molecules cluster around the solute molecules. The solvent in the supercritical fluid can also be referred to as the cosolvent, since the supercritical fluid itself is acting as a solvent. The weight percentage of solvent (or cosolvent) and solute added to the supercritical fluid is preferably from about 1% to about 20%, more preferably from about 5% to about 15%. The amount of solute present is an amount sufficient for critical clusters to form and typically the solute is more dilute than the solvent (or cosolvent).

FIG. 1 illustrates a molecular simulation of forty-eight 2-butanol molecules clustered about a single phenol blue molecule in supercritical carbon dioxide. If the solvent accessible surface of the phenol blue molecule 1 is treated as a large sphere, then the solvent molecules 2 are seen to cluster in a cubic array with a high degree of polar alignment. This polar alignment can influence the dipole moment of the encaged solute molecule causing charge separation within the molecule which ultimately increases the solvent accessible surface to include several smaller overlapping spherical surfaces about the individual atoms of the solute. The cluster in this figure is shown to undergo restructuring 3 and the solute molecule is shown to undergo charge separation 4.

The present invention utilizes critical clusters using substantially optically-pure chiral solvents for asymmetric synthesis reactions whereby a chiral product is formed from achiral reactants. Moreover, the chiral center formed is optically active which is described hereinafter as an optically active chiral center. Molecules with an optically active chiral center has at least 51% of one enantiomeric form of a particular molecule, preferably at least 75% of one enantiomic form of a particular molecule, more preferably at least 90% of one enantiomeric form of a particular molecule.

Critical clusters can affect the spatial orientation of solute molecules encaged by substantially optically-pure chiral solvent molecules. In addition, by affecting the spatial orientation of encaged solute molecules during a chemical reaction, the enantiomeric purity of the product can be affected as well. The ability of critical clusters to influence spatial orientation of the solute molecules is through a unique form of hydrogen-bonding of the substantially optically-pure chiral solvent molecules called multipoint hydrogen bonding. Multipoint hydrogen bonding by chiral solvent molecules to the encaged solute molecules causes the encaged solute molecules to be spatially orientated such that an optically active product results when the encaged solute molecules react.

An example of multipoint hydrogen bonding is when a hydroxyl group of a secondary alcohol hydrogen bonds to an anionic site of a molecule thereby weaking the alpha C-H bond of the secondary alcohol which causes it to hydrogen bond to a second site on the same molecule. Multipoint hydrogen bonding is further described in *Bucciarelli* et al, J.Org. Chem. 1983, 48, 2640–2644, which is incorporated herein by reference.

Figure 2:
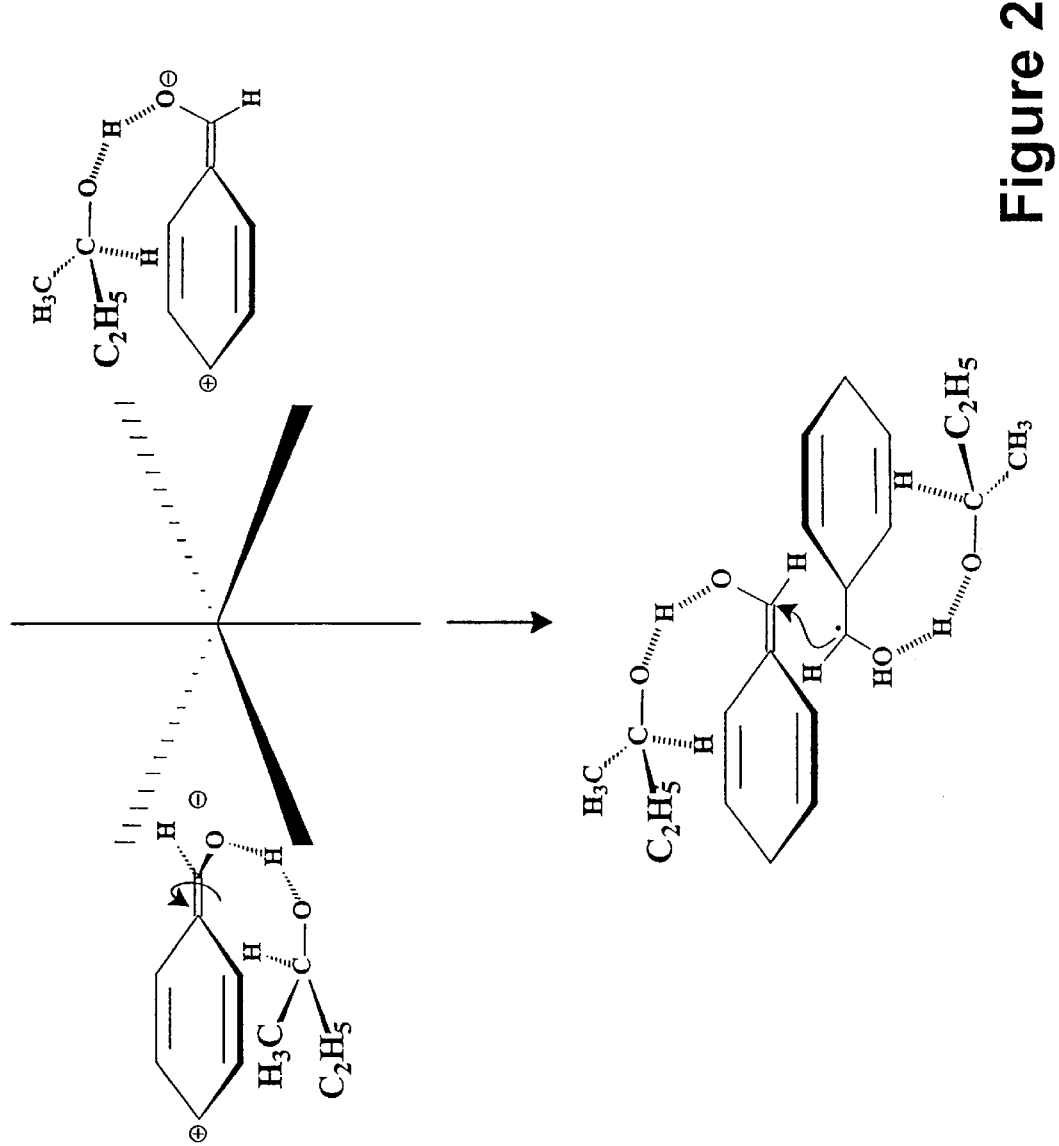
FIG. 2—illustrates two-point hydrogen bonding association in a benzaldehyde molecule induced by a 2-butanol chiral critical cluster.

The substantially optically-pure chiral solvent molecule of choice is a secondary alcohol, since secondary alcohols are capable of multipoint hydrogen bonding. The smaller the carbon chain of the secondary alcohol, the better the secondary alcohol can hydrogen bond. For multipoint hydrogen bonding, the secondary alcohol preferably has at least four carbon atoms and not more than about nine carbon atoms. The preferred secondary alcohol molecule is 2-butanol. The secondary alcohol molecules are preferably selected from the group consisting of S(+)-2-butanol and R(−)-2-butanol. 2-butanol, when used as the solvent, has the ability for two point hydrogen bonding as illustrated in FIG. 2.

The supercritical fluid of the present invention is preferably under conditions of pressure and temperature that do not adversely affect the solute molecules undergoing a chemical reaction. The preferred source of supercritical fluid is carbon dioxide ($CO_2$). The weight percentage of cosolvent and solute added to the supercritical fluid is preferably from about 1% to about 20%, more preferably from about 5% to about 15%. The pressure of the carbon dioxide under supercritical conditions is preferably maintained from about 71 bar to about 275 bar, more preferably from about 100 bar to about 150 bar. The temperature of the carbon dioxide under supercritical conditions is preferably maintained from about 31° C. to about 125° C., more preferably from about 50° C. to about 70° C. The temperature and pressure of the supercritical fluid can be varied to change charge distribution in the solute molecules.

The solute molecule of the present invention can be any molecule capable of forming an optically active chiral center. The solute molecule is preferably a reactant for an asymmetric synthesis reaction. The solute molecule can undergo any chemical reaction to form an optically active center, which optionally can be catalyzed by enzymes, chemicals, light, pH, or temperature.

In one embodiment, the solute molecule is benzaldehyde. When benzaldehyde solute molecules are encaged by optically active chiral solvent molecules in supercritcal fluid, benzaldehyde can undergo photochemical condensation to form S(+)benzoin. When the solvent used is 2-butanol, the 2-butanol undergoes a 2-point hydrogen bonding association as shown in FIG. 2.

Initial hydrogen-bonding of 2-butanol occurs at the anionic oxygen site within the plane of symmetry of benzaldehyde. It is believed that the chiral solvent molecules rock out-of-plane to interact with the pi-electrons of the ring. This rocking action is either to the rectus or sinister faces of the benzaldehyde plane of symmetry, depending on the chirality of the solvent. The only difference between S(+) and R(−)-2-butanols is the reversal of the spatial orientation of the methyl and ethyl groups attached to the asymmetric carbon site. The condensation of benzaldehyde as a result yields S(+)benzoin, a very specific chiral product. The percentage of S(+)benzoin formed is preferably greater than 60%, more preferably greater than 75% and most preferably greater than 90%.

The ability of solvent molecules to cluster around a solute molecule stems from the influence of pressure and temperature on fluid compressibility. Supercritical fluids are most compressible at or near their critical point, primarily their critical pressure. Optimal clustering of 2-butanol around benzaldehyde occurs at from about 100 bar pressure to 150 bar pressure at 50° C., which is the photolysis temperature of benzaldehyde. If higher operating temperatures up to 125° C. is used, than higher operating pressures are needed to sustain the critical state of the fluid.

The present invention also provides a method for directing the position of bonding between a solute molecule and a ligand. In this method, a solute molecule and a ligand are encaged by polar solvent molecules in a supercritcal fluid to form a critical cluster. The supercritical fluid is under conditions of temperature and pressure sufficient to change electric charge distribution in the solute molecule. The bonding of the ligand to the molecule can be optionally catalyzed by enzymes, chemicals, pH, light or temperature.

In one embodiment, the polar solvent molecules can be capable of multipoint hydrogen bonding to the solute molecule, and they can also be chiral. When the chiral solvent molecules are substantially optically-pure, they can form spatially orientated solvent clusters that can result in optically active chiral products when the solute molecule reacts within the critical cluster.

The polar solvent molecules can be secondary alcohol molecules. The secondary alcohol molecules preferably have from four to about nine carbon atoms. The secondary alcohol molecules can be selected from the group consisting of S(+)-2-butanol and R(−)-2-butanol.

A preferred solvent in this embodiment for directing the position to which ligands bond to molecules is acetonitrile. To control the reaction position and control the spatial orientation of the ligand to yield optically active chiral products, a substantially optically-pure chiral polar solvent capable of multipoint hydrogen bonding is preferred. These polar solvent molecules are preferably secondary alcohol molecules. The secondary alcohol molecules preferably have from four to about nine carbon atoms. The secondary alcohol molecules can be selected from the group consisting of S(+)-2-butanol and R(−)-2-butanol.

The supercritical fluid is preferably under conditions of pressure and temperature that do not adversely affect the solute molecules undergoing a chemical reaction. The preferred source of supercritical fluid is carbon dioxide ($CO_2$). The weight percentage of cosolvent and solute added to the supercritical fluid is preferably from about 1% to about 20%, more preferably from about 5% to about 15%. The temperature and pressure of the supercritical fluid can be varied to change the charge distribution in the solute molecules.

Changing the charge distribution of molecules in critical clusters can activate specific sites of these molecules to influence the outcome of a chemical reaction. In one embodiment, the chemical reactivities of the nitrogen and oxygen sites on ritalinic acid in a critical cluster are affected by adjusting the temperature and pressure so that the drug, ritalin, also known as methylphenidate, can be synthesized in one step.

Ritalinic acid possesses two chiral carbon centers indicated by the stars in the structure below, and thus can exist as two separate diasteriomers (erythro and threo) each possessing a (d) and (l) enantiomeric form that are optical isomers.

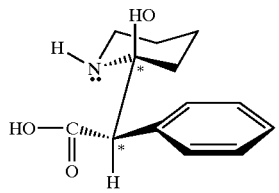

The pharmaceutical drug that is manufactured is the threo form and is typically produced as a racemic mixture of the (d) and (l) enantiomers. The (d) threo enantiomer is the form of the drug that provides therapeutic action related to treating attention deficit disorder.

The charges of ritalinic acid are separated in a critical cluster using polar solvent molecules so that the bonding of a methyl group is directed to the oxygen site of the carboxyl group instead of the amino group. This eliminates the need to protect and deprotect the amine group of ritalinic acid. The pressure of the supercritical fluid is preferably maintained from about 71 bar to about 275 bar, more preferably from about 100 bar to about 150 bar. The temperature of the supercritical fluid is preferably maintained from about 31° C. to about 125° C., more preferably from about 50° C. to about 70° C. The methyl group can come from a methylhalide selected from the group consisting of methylbromide and methyliodide. Any polar solvent capable of inducing charge separation in ritalinic acid would be suitable. The preferred solvent for this embodiment is acetonitrile and the preferred supercritical fluid is carbon dioxide. The one step synthesis of ritalin from ritalinic acid performed by influencing charge separation is illustrated by the following:

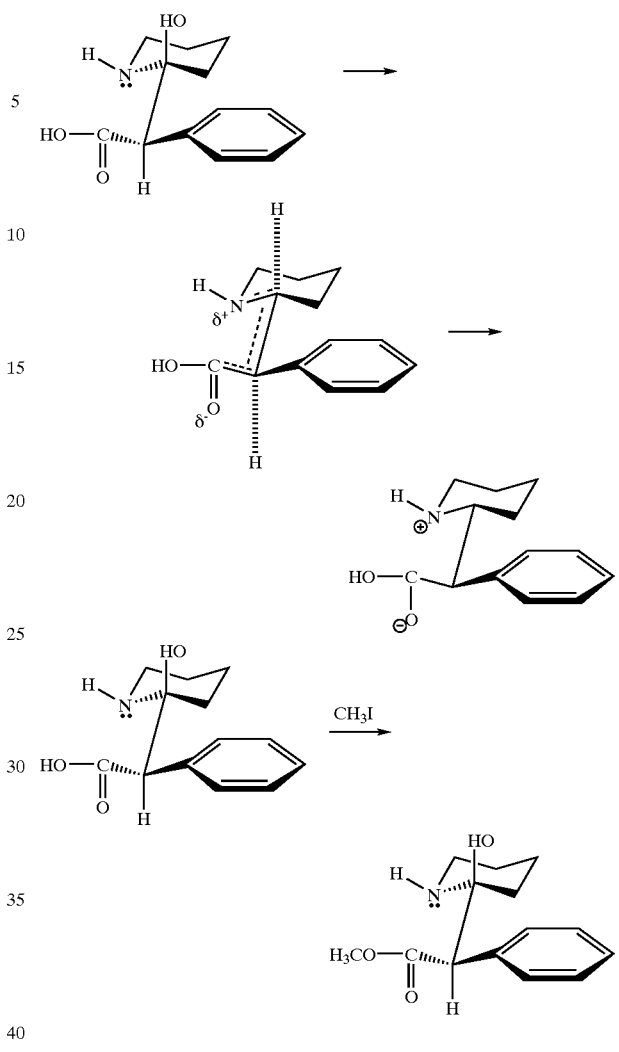

In the one step synthesis of ritalin shown above, the optical purity of the product can be enhanced by choosing a substantially optically-pure chiral solvent capable of multipoint hydrogen bonding.

In another embodiment, the solute molecule is benzylamine and the ligand is an alkylhalide. Under ordinary reaction conditions in liquid, the alkyl group bonds to the amine group 100% of the time. But in a critical cluster, the position to which the alkyl group bonds can be directed to the ortho, para and meta posititions of the benzene ring, and also the alpha position of benzylamine as shown and discussed more fully below in Example 11. The reaction in this embodiment is preferably carried out at a temperature from about 31° C. to about 125° C., more preferably from about 50° C. to about 70° C., and at a pressure preferably from about 71 bar to about 275 bar, more preferably from about 100 bar to about 150 bar. The most preferred conditions are at about 95° C. and 138 bar.

The invention is also a method of making a pharmaceutical compound using critical clusters wherein a ligand and a solute molecule capable of forming a chiral center are encaged by polar solvent molecules in a supercritical fluid under conditions of pressure and temperature sufficient to control electric charge distribution of the solute molecule. The solute molecule and ligand are then reacted whereby the ligand bonds to the solute molecule forming a chiral center.

The polar solvent molecules can be chiral molecules and they can also be substantially optically-pure. In addition, the polar solvent molecules can be capable of multipoint hydrogen bonding. Substantially optically-pure chiral solvent molecules capable of multipoint hydrogen bonding can form highly orientated solvent clusters that can result in an optically active chiral product when the solute reacts in the critical cluster. The polar solvent molecules can be secondary alcohol molecules. The secondary alcohol molecules preferably have from four to about nine carbon atoms. The secondary alcohol molecules can be selected from the group consisting of S(+)-2-butanol and R(−)-2-butanol.

The supercritical fluid that is preferred is under conditions of pressure and temperature that do not adversely affect the solute molecules undergoing a chemical reaction. The preferred source of supercritical fluid is carbon dioxide ($CO_2$). The weight percentage of cosolvent and solute added to the supercritical fluid is preferably from about 1% to about 20%, more preferably from about 5% to about 15%. The temperature and pressure of the supercritical fluid can be varied to change charge distribution in the solute molecules.

In one embodiment, amphetamine can be made when the solute molecule is phenylethylamine and the ligand is a methyl group supplied by a methylhalide selected from the group consisting of methyliodide and methylbromide. Under ordinary reaction conditions in liquid, the methyl group bonds to the amine group 100% of the time. But in a supercritical cluster, a chiral product can be formed by making the methyl group bond to the alpha position of phenylethylamine to make amphetamine. The reaction which forms the chiral product in this embodiment is preferably at a temperature from about 31° C. to about 125° C., more preferably from about 50° C. to about 70° C., and at a pressure preferably from about 71 bar to about 275 bar, more preferably from about 100 bar to about 150 bar. The most preferred conditions are at about 95° C. and 138 bar.

The invention also provides a method for racemic resolution using critical clusters. This method involves encaging racemic mixtures of solute molecules with substantially optically-pure chiral solvent molecules in a supercritical fluid under conditions of temperature and pressure sufficient to form critical clusters. The solvent molecules are capable of multipoint hydrogen bonding with the solute molecules. The encaged solute molecules are then nonenzymatically reacted to enhance the optical purity of the solute molecules.

The racemic resolution reactions in this invention involves changing the pressure and temperature of the supercritical fluid which change the charge distribution of the encaged solute molecules. When the charge distribution passes through a chiral center of the solute molecules, it loses its chirality to form an achiral intermediate. The achiral intermediate then reforms into one enantiomer of the racemic mixture as a result of being spatially orientated by the substantially optically-pure chiral solvent molecules.

In a preferred embodiment, the substantially optically-pure chiral solvent molecules are secondary alcohol molecules. The secondary alcohol molecules preferably have from four to about nine carbon atoms. More preferably, the secondary alcohol molecules are selected from the group consisting of S(+)-2-butanol and R(−)-2-butanol.

In a preferred embodiment, the supercritical fluid that is employed with the method for racemic resolution using critical clusters is carbon dioxide. The supercritical carbon dioxide is preferably maintained at a pressure from about 71 bar to about 275 bar, more preferably from about 100 bar to about 150 bar, and at a temperature from about 31° C. to about 125° C., more preferably from about 50° C. to about 70° C.

In another embodiment, the conditions of temperature and pressure of the supercritical fluid can be made sufficient to change the electric charge distribution of the solute molecule. The weight percentage of cosolvent and solute in the supercritical fluid is preferably from about 1% to about 20%, more preferably from about 5% to about 15%.

The racemic starting material can be a pharmaceutical compound which can be converted by the method of the present invention to form one enantiomer over the other. In one embodiment, the racemic starting material can be a racemic mixture of (dl) threoritaline. One optical isomer of threo ritalin can then be made from the mixture by the racemic resolution reaction of the present invention.

EXAMPLES

The following examples have been set forth below as a guide to the practitioner, and are not meant in any way to limit the scope of the present invention.

Example 1

The solvatochromic behavior of the organic dye phenol blue was compared using various polar and nonpolar solvents mixed in supercritical carbon dioxide. The technique used for the comparison was high-pressure UV/visible spectroscopy.

Figure 3:
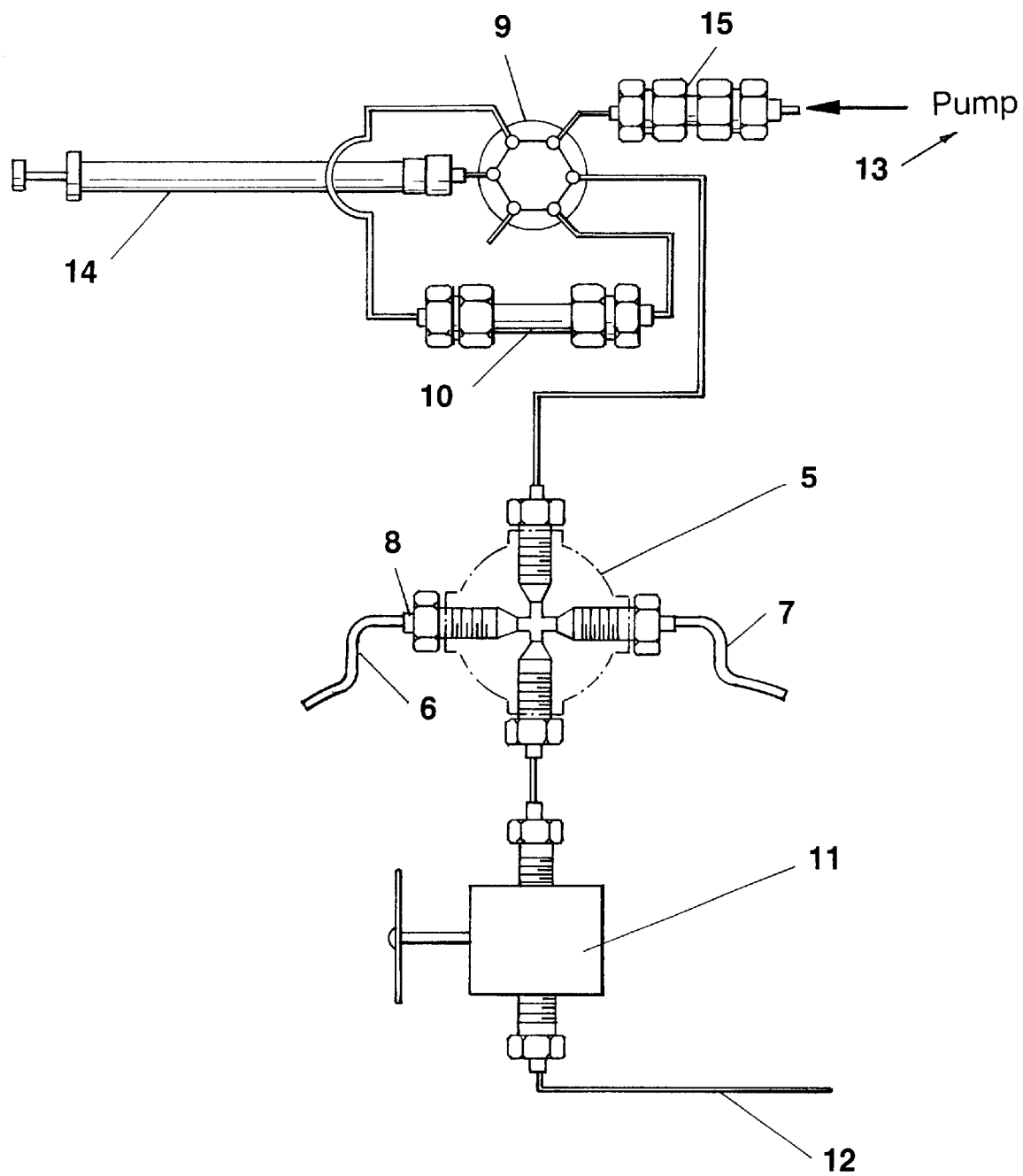
FIG. 3—is a schematic of an optical cell apparatus having a cell volume of 0.74 $\mu L$.

Referring to FIG. 3, an optical cell 5 was constructed from a 1/16 inch outer diameter (o.d.) stainless steel tubing which was connected to the cell using standard HPLC fittings. The internal bore of the cell was enlarged from 250 microns to 685 microns to yield a cell volume of 0.74 $\mu L$. The pathlength of the cell was 2 mm. Fiber optics (Ceram Optec Inc.) were used to bring light into 6 and out of 7 the cell. The fibers were 600 micron o.d., but were coated with a silica cladding and polyimide buffer to maximize light throughput. The total outer diameter of the fiber was 710 microns. The bare-end of the fiber was polished so that no imperfections were observed at 40×magnification. The fibers were mounted into the cell using polyetheretherketone (PEEK) tubing sleeves 8 and standard high performance liquid chromatography (HPLC) fittings. The other ends of the fibers were fitted with standard (SMA) connectors. The SMA 906 connector has a precision alignment sleeve and is of the threaded mating mechanism design to easily interface the fiber-optics with the light source and detector.

The sample was introduced into the cell using a Rheodyne (7010) HPLC injection valve 9. 5 $\mu L$ samples of phenol blue dissolved in the organic cosolvent were introduced through the injector valve and into a 2 ml volume mixing loop 10. The loop was made out of a 1/16 inch o.d. stainless steel tubing which had an inner bore of 250 microns. The samples were allowed to mix with the supercritical fluid and flow through the cell simultaneously. This allowed air in the loop to be displaced. The outlet of the cell was connected to a two-way high-pressure (690 bar rated, Scientific Instruments Inc.) valve 11 and a pressure restrictor 12. The restrictor 12 was constructed by crimping a 10 cm length of a 1/16 inch o.d. stainless steel tube at the end. This tube had a 50 micron bore. The crimping was maintained at a 1.5 ml/minute flow rate at 300 bar pressure. The optical cell and valves were maintained at 50° C.±2° C. by building all the components inside of an Eppendorf HPLC column heater.

The system was pressurized using a syringe pump 13 (Isco Inc, model 260D) which is capable of delivering up to 750 bar pressure. A check valve 15 was located at the liquid carbon dioxide inlet to prevent backflow. Liquid carbon dioxide used to fill the pump was purchased from Scott Specialty Gas, Inc.

The spectrometer was comprised of a deuterium/tungsten-halogen light source from Analytical Instruments and a fiber-optic UV-Visible spectrometer (Ocean Optics Inc. model ST-2000) that was capable of scanning from 180 m to 800 m with an optical resolution of 0.2 m. A WIN pentium computer was used in conjunction with Ocean Optics software for data acquisition.

To calibrate the system, a standard solution of phenol blue and methanol was prepared yielding a concentration of 0.80 mg/ml. The cell was pressurized to 200 bar and the temperature was set to 50° C. Samples ranging from 1 μL to 50 μL of 0.8 mg/ml phenol blue-methanol solution were injected into the system via a sample introduction injector 14, and the $\gamma_{max}$ of absorbency was recorded and graphed using Microsoft Excel to test for linearity. The cell was pressurized to 100 bar and closed off with sample loaded in the cell. The $\gamma_{max}$ of absorbency was recorded at 15-minute intervals over the period of 1 hour. A horizontal line appeared when the data was plotted.

Standard solutions of 0.4 mg of phenol blue and 1 ml of an organic solvent were prepared and used throughout the study. All chemicals were purchased from the Aldrich Chemical Co., and used without further purification. 5 μL samples of each solution were injected into the system where it was mixed with the supercritical carbon dioxide. In all experiments, identical procedures were followed for sample introduction.

Figure 4:
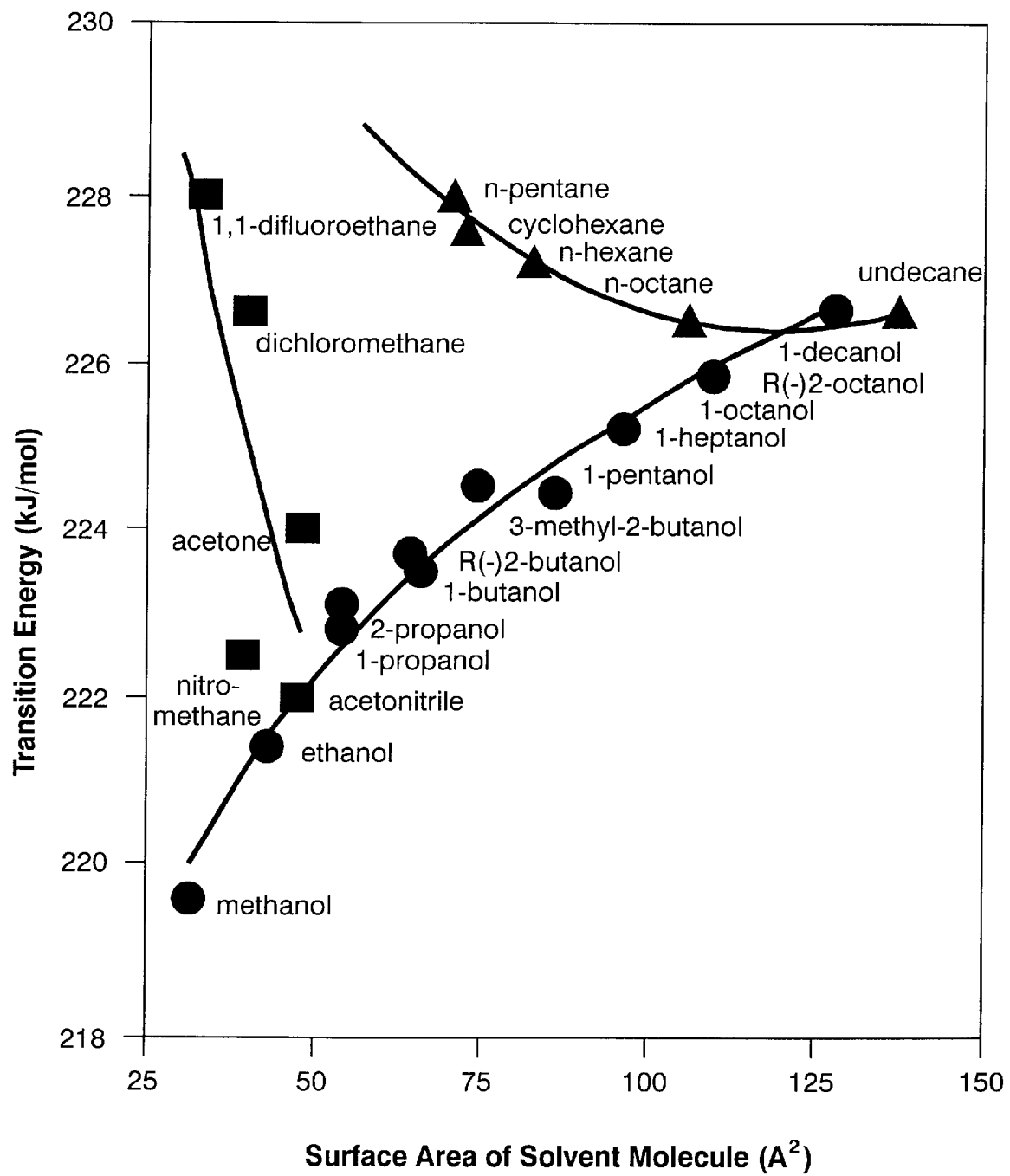
FIG. 4—is a graph showing a comparison of the solvatochromic behavior of the organic dye phenol blue in the presence of various polar and nonpolar solvents mixed in supercritical carbon dioxide at a pressure of 100 bar.
Figure 5:
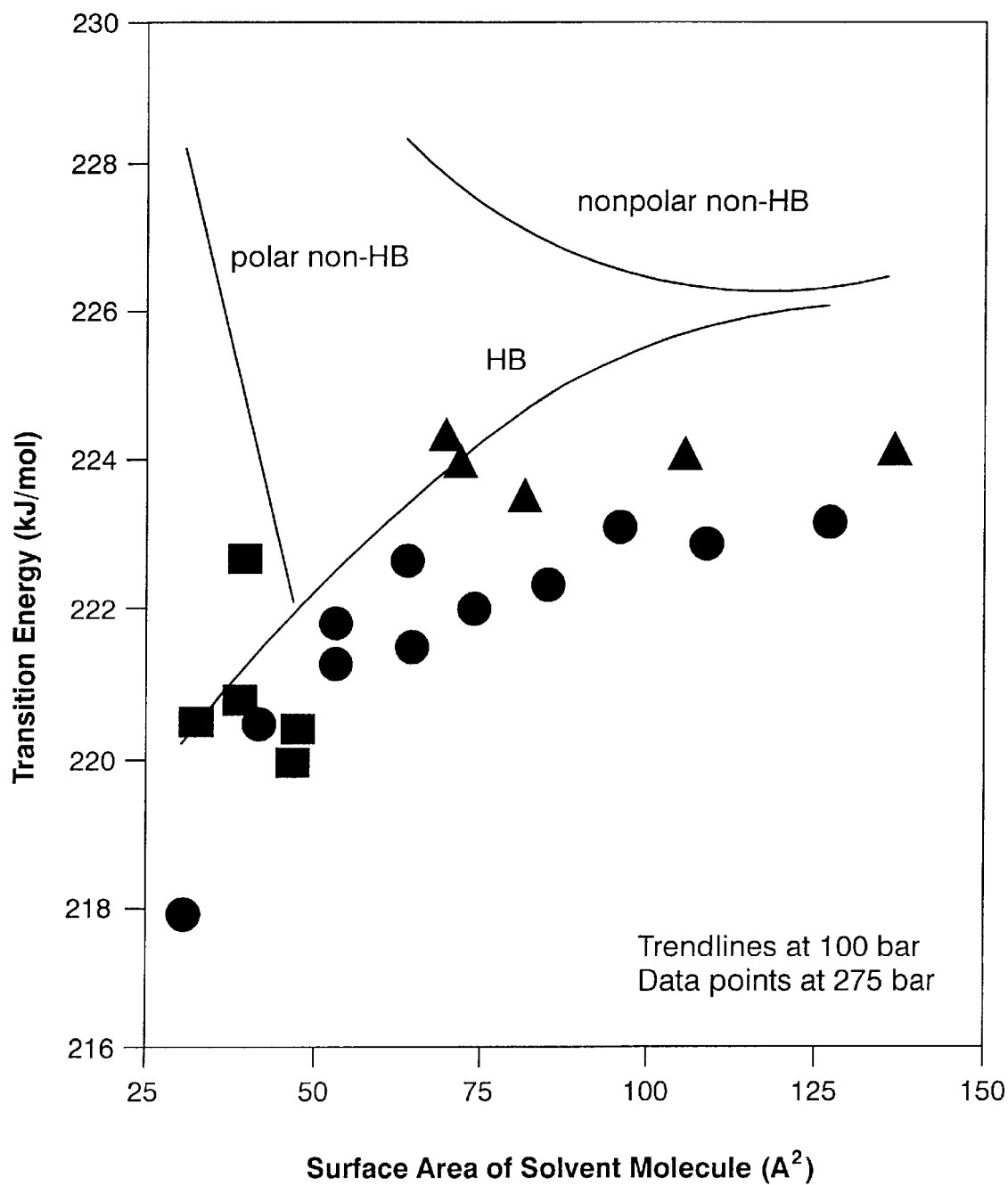
FIG. 5—is a graph showing a comparison of the solvatochromic behavior of the organic dye phenol blue in the presence of various polar and nonpolar solvents mixed in supercritical carbon dioxide at a pressure of 275 bar.

The results shown in FIGS. 4 and 5 show the solvatochromic behavior of phenol blue at 100 bar pressure in FIG. 4, which is close to the critical point of carbon dioxide, and at 275 bar pressure in FIG. 5. FIG. 4 shows that the larger the carbon chain of the secondary alcohol, the higher the transition energy. When there is more intimate hydrogen bonding between solvent molecules and phenol blue, the transition energy is lower. Therefore, there is less intimate hydrogen bonding when secondary alcohols of larger carbon chains are used as solvents. FIGS. 4 shows a delineation of polar and nonpolar solvents at 100 bar. This delineation implies clustering of solvent molecules at about the critical point of carbon dioxide. At 275 bar, well above the critical point of carbon dioxide, there is less delineation for the different solvent molecules, as shown in FIG. 5, which implies less clustering.

Example 2

The solvatochromic behavior of the organic dye phenol blue was compared using solvent S(+) and R(−)-2-butanol and S(+) and R(−)-2-octanols. The technique used for the comparison was the same as in EXAMPLE 1.

Figure 6:
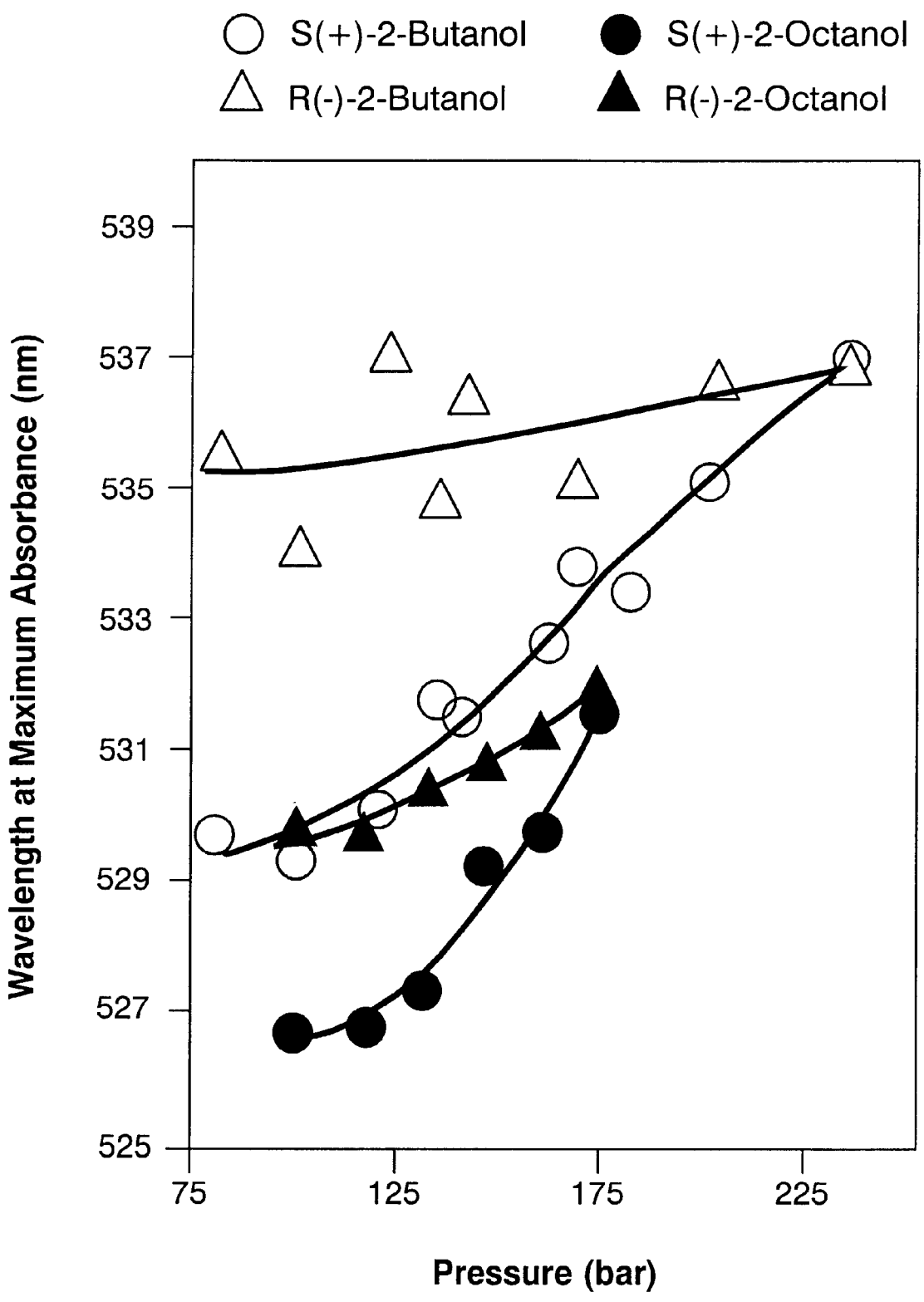
FIG. 6—is a graph showing a comparison of the solvatochromic behavior of the organic dye phenol blue in the presence of S(+) and R(−)-2-butanols and S(+) and R(−)-2-octanols in supercritical carbon dioxide as a function of pressure.

The results are shown in FIG. 6. These results show the differences of the solvatochromic behavior of phenol blue at pressures near the critical pressure of the fluid mixture. The fluid mixture was comprised of 5% organic solvent in supercritical carbon dioxide. At pressures at or near the critical pressure of carbon dioxide, there is greater delineation of the chiral solvent molecules. As in the above example, this implies clustering of solvent molecules at or near the critical pressure of carbon dioxide.

Example 3

This example illustrates the ability to use critical clusters for condensing achiral benzaldehyde to form optically active S(+)benzoin.

Figure 7:
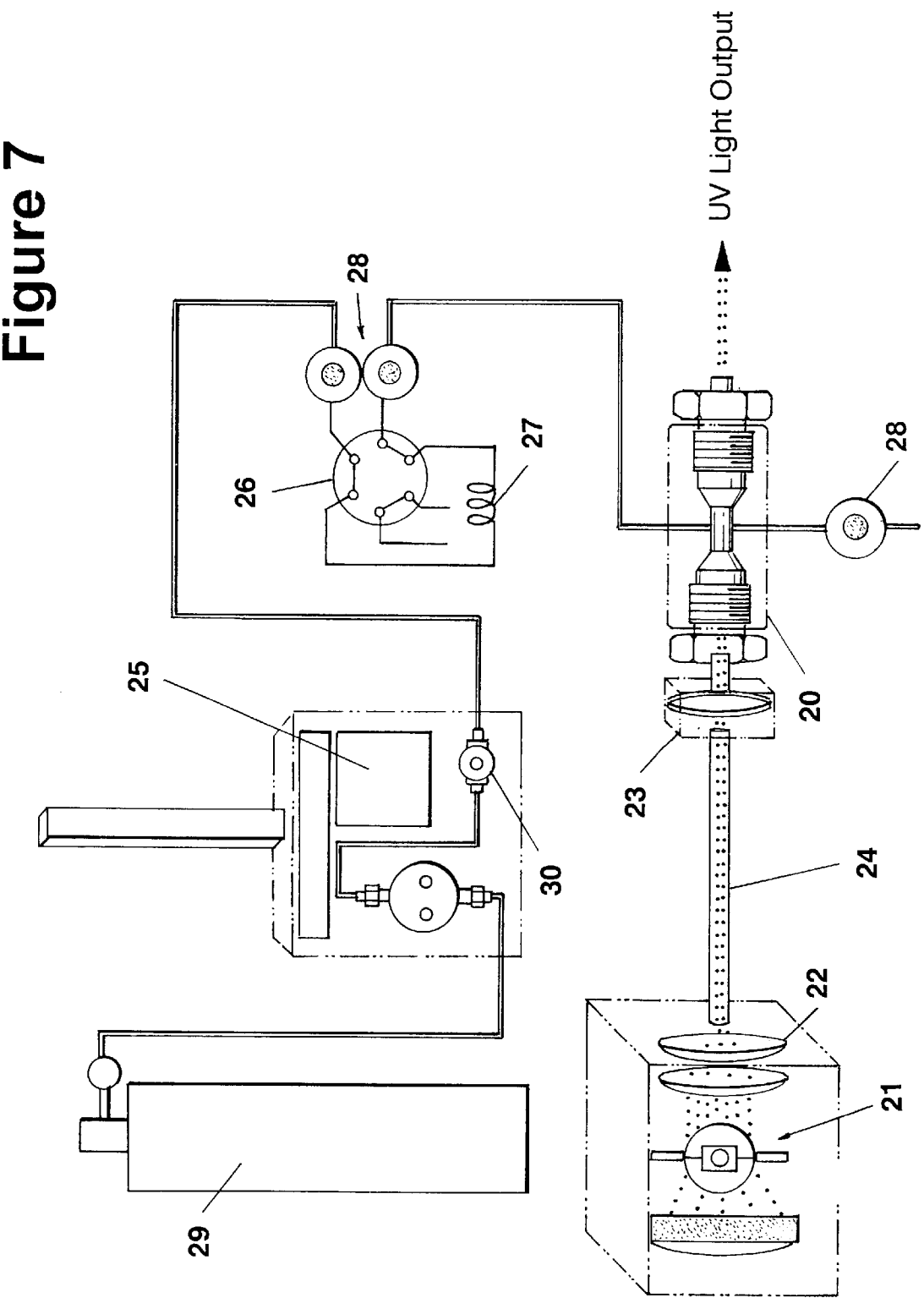
FIG. 7—is a schematic of an optical cell apparatus used in the condensation reaction of benzaldehyde.

The cell used in this Example is illustrated in FIG. 7. Referring to FIG. 7, a high pressure optical cell 20 was used which was capable of sustaining supercritical fluid pressures up to 350 bar and temperatures to 125° C. The cell was equipped with both entrance and exit sapphire windows and was sealed onto a stainless steel reactor housing through Teflon gaskets which yielded an active volume of 16 μL. Ultraviolet light was allowed to enter and exit the cell so that light input to the cell could be maximized by adjusting the focusing lens position. The ultraviolet light source consisted of an unfiltered high pressure mercury arc lamp 21 (Osram Inc., 500 watt lamp) whose light outlet was focused through reflection from a parabolic mirror 22 onto an additional focusing lens 23 which maximized the photon flux into a 2 mm diameter fiber optic bundle 24 (Oriel, Inc,). The light was again refocused to a 1 mm spot just prior to entering the cell. Any UV light source with focussing optics would be appropriate for this action. Cell temperatures were maintained to within 2° C. through four restive cartridge heaters (OMEGA, Inc.) mounted within an outer plastic housing and controlled through feedback from a platinum resistance electrode. System pressures were maintained through an Isco syringe pump 25 (model 260D) designed for operation with supercritical fluid extractors. The pump was capable of operating at constant pressure. Sample was introduced in one of two ways; either through a high pressure Rheodyne injection valve 26 (model 7010) with a 20 μl volume sample loop 27, or through two Valco 3-way high-pressure valves 28. In the later method, the cell was completely filled with sample and excess allowed to flow out through a cell waste line.

A stock solution was prepared using benzaldehyde in chiral S(+)-2-butanol solvent to yield a concentration of 50 μg/μL. The benzaldehyde and chiral S(+)-2-butanol were purchased from Aldrich, Inc. The supercritical fluid source 29 was pure carbon dioxide which was purchased from Scott Specialty Gases, Inc. The Isco model 260D syringe pump 25 was preloaded with liquid carbon dioxide to capacity then the pump's cylinder head was prepressurized to the operating pressure of the reaction. The operating pressure of the reaction was 69 bar. The cylinder head was equipped with a water jacket to maintain fluid temperatures within it at 35° C. The pump outlet valve leading to the sample injector and optical cell was closed during this procedure and were initially at atmospheric pressure.

Approximately 5 μL of the benzaldehyde stock solution were introduced into the system via the Rheodyne injection valve 26. The total secondary alcohol concentration was adjusted to maintain bulk loading of co-solvent at a constant 5% throughout the measurements. Once loaded, the injection valve 26 was actuated and the pump outlet valve opened. The sample was displaced from the loop into the cell for photolysis. A check valve 30 was located at the inlet to the injector valve to prevent sample back-flow.

Photolysis was typically carried out for 20 minutes at 50° C. Samples were then extracted by depressurization of the cell through a 0.5 meter by 50 micron internal diameter silica capillary tube into 1 ml of acetone solvent.

The samples were concentrated to 200 μL volumes, and 1 μL aliquots were analyzed by capillary gas chromatography (GC) using a flame ionization detector (FID) on a Hewlett Packard 5890 instrument. A 30 m×0.25 mm i.d. Chiraldex-β column (Altech Associates, Inc.) was used for chiral product separation.

The GC method included the following: The injector was maintained at 225° C.; the FID was maintained at 350° C.; the column head pressure with helium carrier gas was maintained at 15 psi; the injection split ratio was 100:1; the column was maintained at 160° C. initially, with no hold time, then temperature programmed to 200° C. at a 3° C./min. rate. Product yields were measured using the FID response, and peak areas (PAU) were calculated using Vision 4 chromatography software (Scientific Systems, Inc.) on a PC computer.

The products of the experiment using S(+)-2-butanol as the solvent at 69 bar pressure were S(+)benzoin at 65±5%; R(−)benzoin at 35±5%; and an enantiomeric excess of 30%.

Example 4

This example illustrates the ability to use critical clusters for the condensing achiral benzaldehyde to form optically active S(+)benzoin.

All the reaction conditions were the same as in EXAMPLE 3 above except that the operating pressure of the experiment was at 138 bar. The products of the experiment using S(+)-2-butanol as the solvent at 138 bar pressure were S(+)benzoin at 92%; R(−)benzoin at 8%; and an enantiomeric excess of 84%.

Example 5

As in the above example, this example also illustrates the ability to use critical clusters for condensing achiral benzaldehyde to form optically active S(+)benzoin.

All of the reaction conditions were the same as in EXAMPLE 3 above except that the operating pressure of the experiment was at 207 bar. The products of the experiment using S(+)-2-butanol as the solvent at 207 bar pressure were S(+)benzoin at 95±1%; R(−)benzoin at 5±1%; and an enantiomeric excess of 90%.

Example 6

As in the above example, this example also illustrates the ability to use critical clusters for condensing achiral benzaldehyde to form optically active S(+)benzoin.

All of the reaction conditions were the same as in EXAMPLE 3 above except that the chiral solvent molecule used was R(−)-2-butanol. The products of the experiment using R(−)-2-butanol as the solvent at 69 bar pressure were S(+)benzoin at 62%; R(−)benzoin at 38%; and an enantiomeric excess of 24%.

Example 7

As in the above example, this example also illustrates the ability to use critical clusters for condensing achiral benzaldehyde to form optically active S(+)benzoin.

All of the reaction conditions were the same as in EXAMPLE 3 above except that the chiral solvent molecule used was R(−)-2-butanol and the operating pressure of the experiment was 138 bar. The products of the experiment using R(−)-2-butanol as the solvent at 138 bar pressure were S(+)benzoin at 96±3%; R(−)benzoin at 4±3%; and an enantiomeric excess of 92%.

Example 8

As a comparision, this example illustrates the ability to use liquid-phase S(+)-2-butanol as a solvent for condensing achiral benzaldehyde to form optically active S(+)benzoin.

Samples were carried out in the liquid phase at 50° C. using a four-faced UV-visible cuvette. 1 ml of S(+)-2-butanol was containing benzaldehyde substrate was photolyzed using the same light source as in Example 3. The cuvette was mounted in a standard commercial mirrored multi-pass holder so that UV light was reflected through the cell several times to optimize light absorption by the sample.

The samples were concentrated to 200 µL volumes, and 1 µL aliquots were analyzed by capillary gas chromatography (GC) using a flame ionization detector (FID) on a Hewlett Packard 5890 instrument. A 30 m×0.25 mm i.d. Chiraldex-β column (Altch Associates, Inc.) was used for chiral product separation. The GC method was the same as in Example 3.

The products of the experiment using S(+)-2-butanol as the solvent were S(+)benzoin at 52±3%; R(−)benzoin at 48±3%; and an enantiomeric excess of 4%.

Example 9

As a comparison, this example illustrates the ability to use liquid-phase R(−)-2-butanol as a solvent for condensing achiral benzaldehyde to form optically active S(+)benzoin.

All of the reaction conditions were the same as in EXAMPLE 8 above except that the chiral solvent molecule used was R(−)-2-butanol. The products of the experiment using R(−)-2-butanol as the solvent were S(+)benzoin at 54%; R(−)benzoin at 46%; and an enantiomeric excess of 8%.

A view of the results of Examples 3–9 reveals that reactions carried out in just the liquid-phase of the chiral secondary alcohols (i.e. Examples 8 and 9) exhibited only a slight enantiomeric excess between 4% and 8%. This behavior is similar to other asymmetric induction reactions carried out in the liquid phase using chiral solvents. Reactions carried out in the cluster phase in Examples 3–7 shows elevations in enantiomeric excess. The extent of this excess can be controlled by the operating pressure of the supercritical fluid yielding near-quantitative excesses.

Example 10

The synthesis of ritalin, also known as methylphenidate, from ritalinic acid presents an example of potential application of critical clusters to drug synthesis through controlling site reactivity.

A stock solution of of 1 µg/µL of threo ritalinic acid in acetonitrile solvent, and a stock solution of 5 µg/µL of methyl iodide in acetonitrile were prepared. A sample comprising a 5 µL of methyl iodide stock and 15 µL of ritalinic acid was injected into a 50 µL loop of a Rheodyne injection valve. These experiments were conducted in the small volume optical cell described in Example 3 using the same methodologies for sample introduction. The reaction was carried out for 30 minutes at 138 bar pressure and 95° C. temperature with UV light. After the reaction, the contents of the cell was collected by depressurizing the cell into a volume of methanol. The sample was concentrated and analyzed by capillary gas chromatography using Hewlett Packard 5890 instrument equipment with a flame ionization detector. Products were separated using a 30 meter×0.25 mm i.d. chiraldex β capillary column. This column had the ability to resolve all four isomers of methyl phenidate.

An analysis of the resulting products reveals that methylation occurs exclusively at the oxygen site resulting in a racemic mixture of (dl) threo methyl phenidate products. In addition, there was no diastereomerization to the erythro isomer.

Example 11

This example demonstrates how to influence chemical reactivity through dipole induction by reacting benzylamine with methyliodide.

Figure 8:
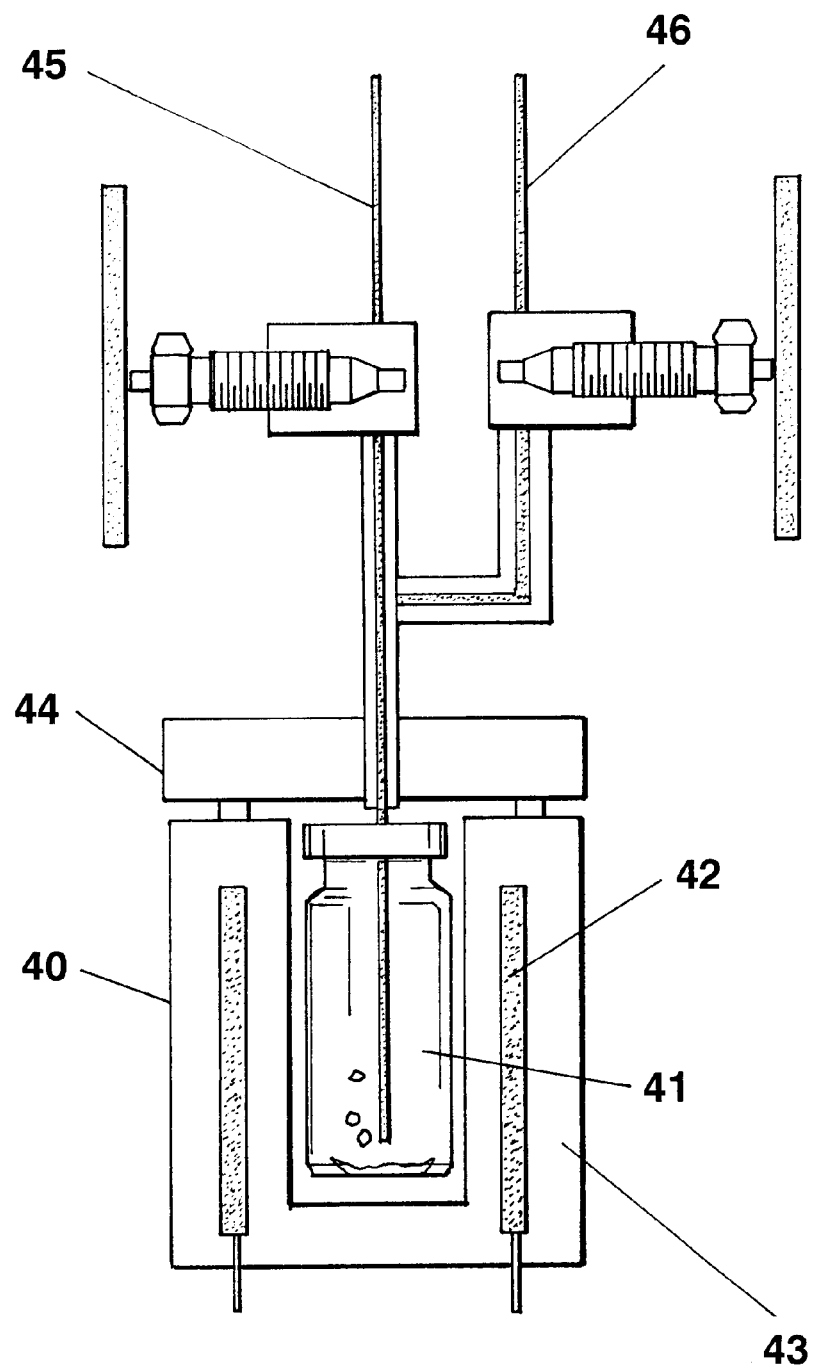
FIG. 8—is a schematic of a large volume supercritical reactor.

Referring to FIG. 8, a large volume supercritical fluid reactor cell 40 was constructed which had a 3 inch o.d. and was bored out to accommodate a standard 10 ml volume Reacti-Vial 41. The cell also had holes bored into the bottom to accommodate four 50 watt (Omega, Inc.) cartridge heaters 42 that were controlled using an Omega series 9000N proportional band controller and thermocouple feedback. Temperatures were controlled to within ±1° C. The top of the cell was pressure seated to the cell body using a Teflon o-ring 43. The cell top was a conventional Conflat flange blank 44 (Valco) and the seal was made with six concentrically space bolts treaded into the body of the cell. Inlet and outlet to the cell was through a single 0.25 inch stainless steel tube that was an integral machined part of the top flange thus eliminating any weld seals. This tube had an insert tube of 0.125 inch o.d. stainless steel which served as the sample inlet.

The cell was interfaced to an Isco 260D supercritical fluid syringe pump using standard high pressure fittings and 1/16 inch o.d. stainless steel tubing. Samples were introduced using a Rheodyne stainless steel HPLC injection valve 45 equipped with a 1 ml sample loop. Samples were introduced in exactly the same manner as described for the benzaldehyde reactions in Example 3 with the exception that the larger volume cell allowed for introduction of larger volumes of starting material dissolved in acetonitrile. In all experiments, a sample mixture of 500 µL of acetonitrile containing 50 µL of benzylamine and 40 µL of methyliodide was injected and pressurized to the appropriate operating pressure using the controls on the supercritical fluid delivery pump. All pressure reactions were carried out at 60° C. under dynamic mode at a 0.09 mL/min flow rate. Liquid phase control reactions were carried out by simply loading the reactant mixture directly into the cell and allowing it to sit for 25 minutes sealed off.

In pressure experiments, the outlet of the cell 46 was connected to a pinched 1/16 inch o.d. stainless steel tube which served as a flow restrictor. The contents of the reaction were collected in methanol and analyzed by capillary gas chromatography using a 5890 Hewlett Packard gas chromatograph equipped with a flame ionization detector. Products were resolved using a 60 m×0.25 mm o.d. amine column (Alltech Associates, Inc.). The chemical reaction in the liquid phase, at 137 bar pressure and at 275 bar pressure, as well as the results of these experiments are shown below.

The results show that in the liquid phase, all methylation occurred at the amine site. However, at 137 bar, charge separation on the benzylamine can redirect site reactivity away from the amine and methylate the alpha position of benzyl amine creating a new chiral center. At 275 bar, the methyl group bonds primarily (84%) to the para position of benzyl amine. These results reveal that site reactivity can be pressure tuned in critical clusters.

Example 12

This example demonstrates how to synthesize amphetamine by influencing chemical reactivity through dipole induction. A cell as described in Example 1.1 can be used to synthesize amphetamine from phenylethylamine and methyliodide. Sample introduction into the cell can also be done in the same manner as in Example 11.

A sample mixture of 500 µL of acetonitrile containing 50 µL of phenylethylamine and 40 µL of methyliodide is injected and pressurized to the appropriate operating pressure using the controls on the supercritical fluid delivery pump. All pressure reactions are carried out at 60° C. under dynamic mode at a 0.09 mL/min flow rate.

The outlet of the cell is connected to a pinched 1/16 inch o.d. stainless steel tube which serves as a flow restrictor. The contents of the reaction are collected in methanol and analyzed by capillary gas chromatography using a 5890 Hewlett Packard gas chromatograph equipped with a flame ionization detector. The product formed is amphetamine.

What is claimed is:

1. A method for asymmetric synthesis using critical clusters comprising the steps of:
   (i) encaging at least one solute molecule with substantially optically-pure chiral solvent molecules in a supercritical fluid under conditions of temperature and pressure sufficient to form critical clusters, said solvent molecules capable of multipoint hydrogen bonding to said solute molecule; and,
   (ii) reacting said encaged solute molecules whereby an optically active chiral center in a product of said reaction is formed.

2. A method for asymmetric synthesis using critical clusters according to claim 1 wherein said substantially optically-pure chiral solvent molecules are secondary alcohol molecules.

3. A method for asymmetric synthesis using critical clusters according to claim 2 wherein said secondary alcohol molecules have from four to about nine carbon atoms.

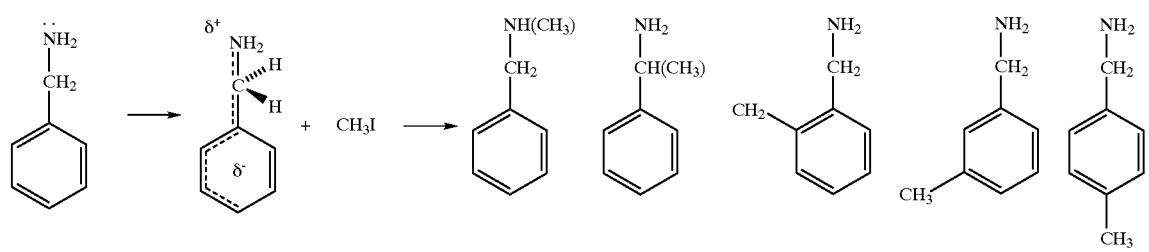

| | | | | | | |
|---|---|---|---|---|---|---|
| Reaction State | | 100% | 0% | 0% | 0% | 0% |
| Cluster (137 bar) | | 0% | 13% | 26% | 29% | 32% |
| Cluster (275 bar) | | 0% | 0% | 10% | 6% | 84% |

4. A method for asymmetric synthesis using critical clusters according to claim 3 wherein said secondary alcohol molecules are selected from the group consisting of S(+)-2-butanol and R(−)-2-butanol.

5. A method for asymmetric synthesis using critical clusters according to claim 1 wherein said supercritical fluid is carbon dioxide.

6. A method for asymmetric synthesis using critical clusters according to claim 5 wherein said supercritical carbon dioxide is maintained at a pressure from about 71 bar to about 275 bar and at temperature from about 31° C. to about 125° C.

7. A method for asymmetric synthesis using critical clusters according to claim 5 wherein said supercritical carbon dioxide is maintained at a pressure from about 100 bar to about 150 bar and at temperature from about 50° C. to about 70° C.

8. A method for asymmetric synthesis using critical clusters according to claim 1 wherein the weight percentage of said solvent and solute in said supercritical fluid is from about 1% to about 20%.

9. A method for asymmetric synthesis using critical clusters according to claim 1 wherein the weight percentage of said solvent and solute in said supercritical fluid is from about 5% to about 15%.

10. A method for asymmetric synthesis using critical clusters according to claim 1 wherein said solute molecule is benzaldehyde.

11. A method for asymmetric synthesis using critical clusters according to claim 10 wherein said product having an optically active chiral center comprises (S)(+)benzoin.

12. A method for asymmetric synthesis using critical clusters according to claim 1 wherein said conditions of temperature and pressure are sufficient to change the electric charge distribution of said solute molecule.

* * * * *